United States Patent [19]

Yarranton et al.

[11] Patent Number: 5,015,573

[45] Date of Patent: May 14, 1991

[54] DNA VECTORS AND THEIR USE IN RECOMBINANT DNA TECHNOLOGY

[75] Inventors: Geoffrey T. Yarranton, Winnersh; Gwynfor O. Humphreys, Wokingham; Martin K. Robinson; Celia A. Caulcott, both of Maidenhead; Edwina M. Wright, Taplow, all of United Kingdom

[73] Assignee: Celltech Limited, Slough, United Kingdom

[21] Appl. No.: 282,960

[22] Filed: Dec. 5, 1988

Related U.S. Application Data

[63] Continuation of Ser. No. 142,281, Dec. 30, 1987, abandoned, which is a continuation of Ser. No. 676,392, Nov. 20, 1984, abandoned.

[30] Foreign Application Priority Data

Mar. 25, 1983 [GB] United Kingdom ................ 8308236

[51] Int. Cl.[5] ...................... C12P 21/00; C12P 19/34; C12P 15/00; C12P 1/20
[52] U.S. Cl. ..................................... 435/69.1; 435/91; 435/172.3; 435/226; 435/252.33; 435/320.1; 935/29; 935/42; 935/72; 935/73
[58] Field of Search ...................... 435/68, 172.3, 320, 435/252.33; 536/27; 935/43, 29

[56] References Cited

U.S. PATENT DOCUMENTS 4,806,471  2/1989  Molin et al. ........................... 435/68

*Primary Examiner*—Thomas Mays
*Attorney, Agent, or Firm*—Cushman, Darby & Cushman

[57] ABSTRACT

A new class of DNA vectors, each comprising two replication systems; a first origin of replication resulting in a low copy number and stable inheritance of the plasmid, and a second, high copy number, origin of replication at which replication is directly controllable such that, when host cells carrying the vector are propagated under a first set of conditions, replication takes mainly from the low copy number origin, and that when said cells are propagated under a second set of conditions, replication takes place also from the high copy number origin to produce a high yield of gene product. The controllable origin of replication may be under the control of a natural promoter of RNA transcription or a substitute promoter such as the PL promoter or lac promoter.

18 Claims, 16 Drawing Sheets

(i)
(ii)
(iii)

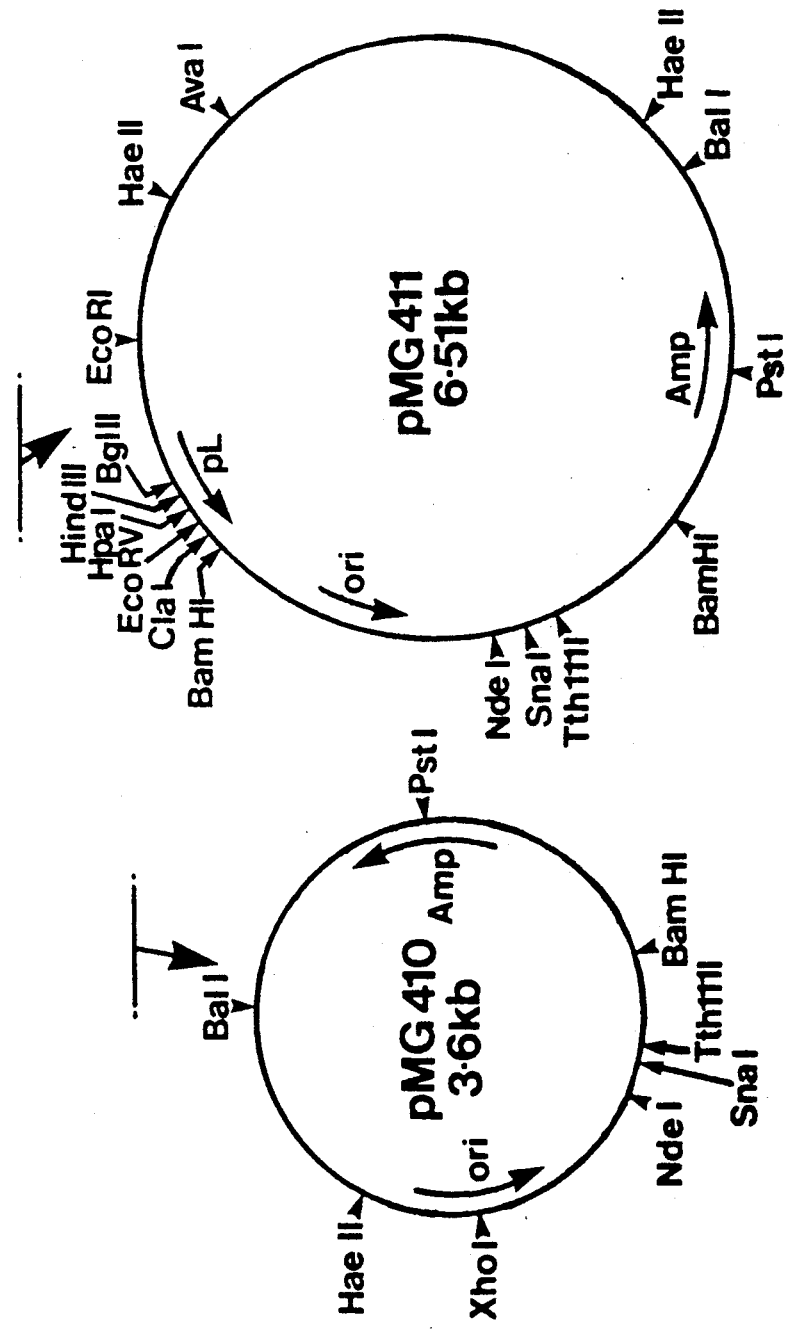
FIG. 1 (iii)

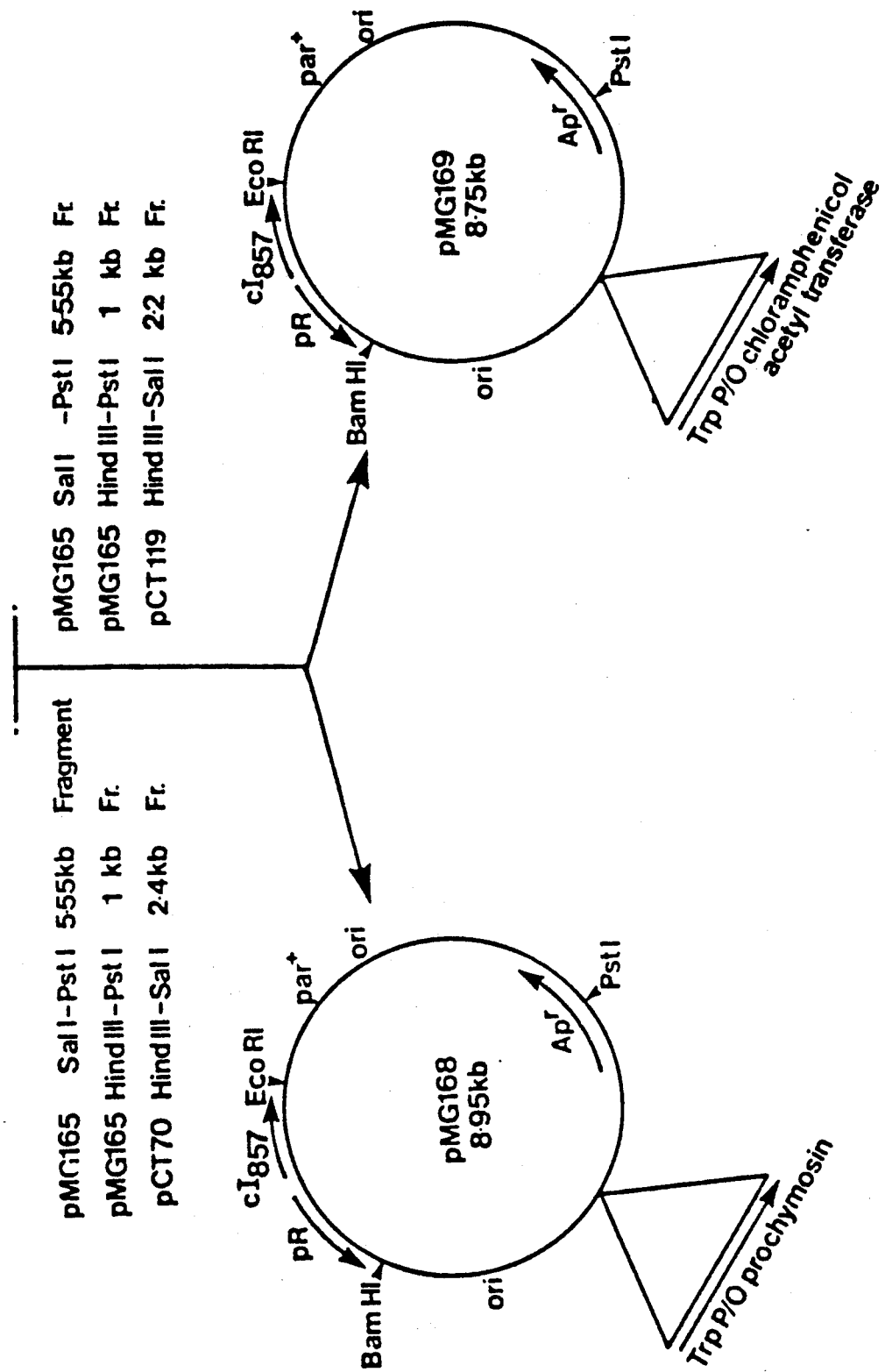
FIG. 3(iii)

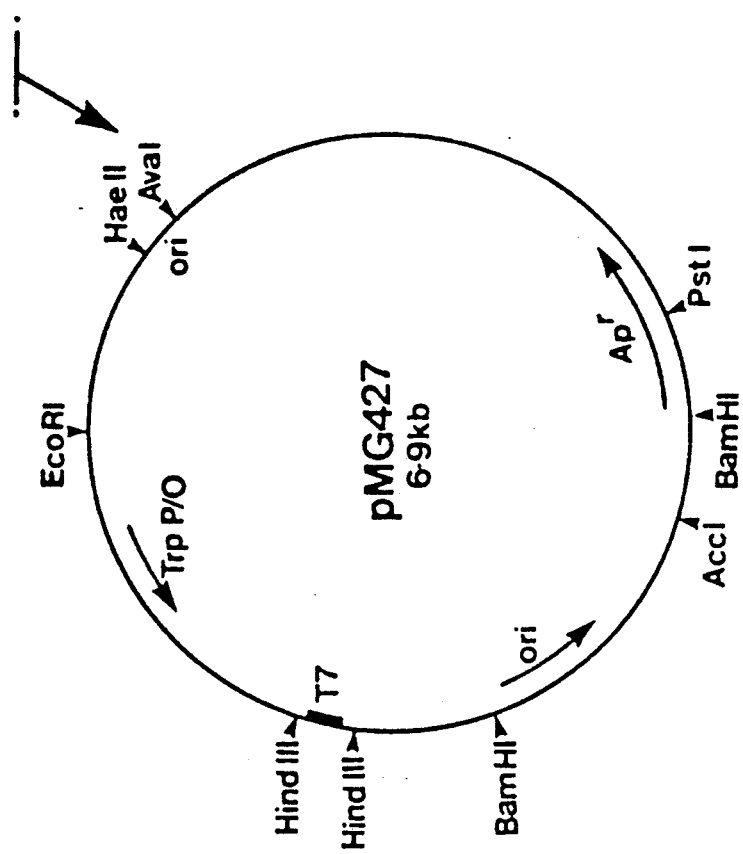
FIG. 5(iii)

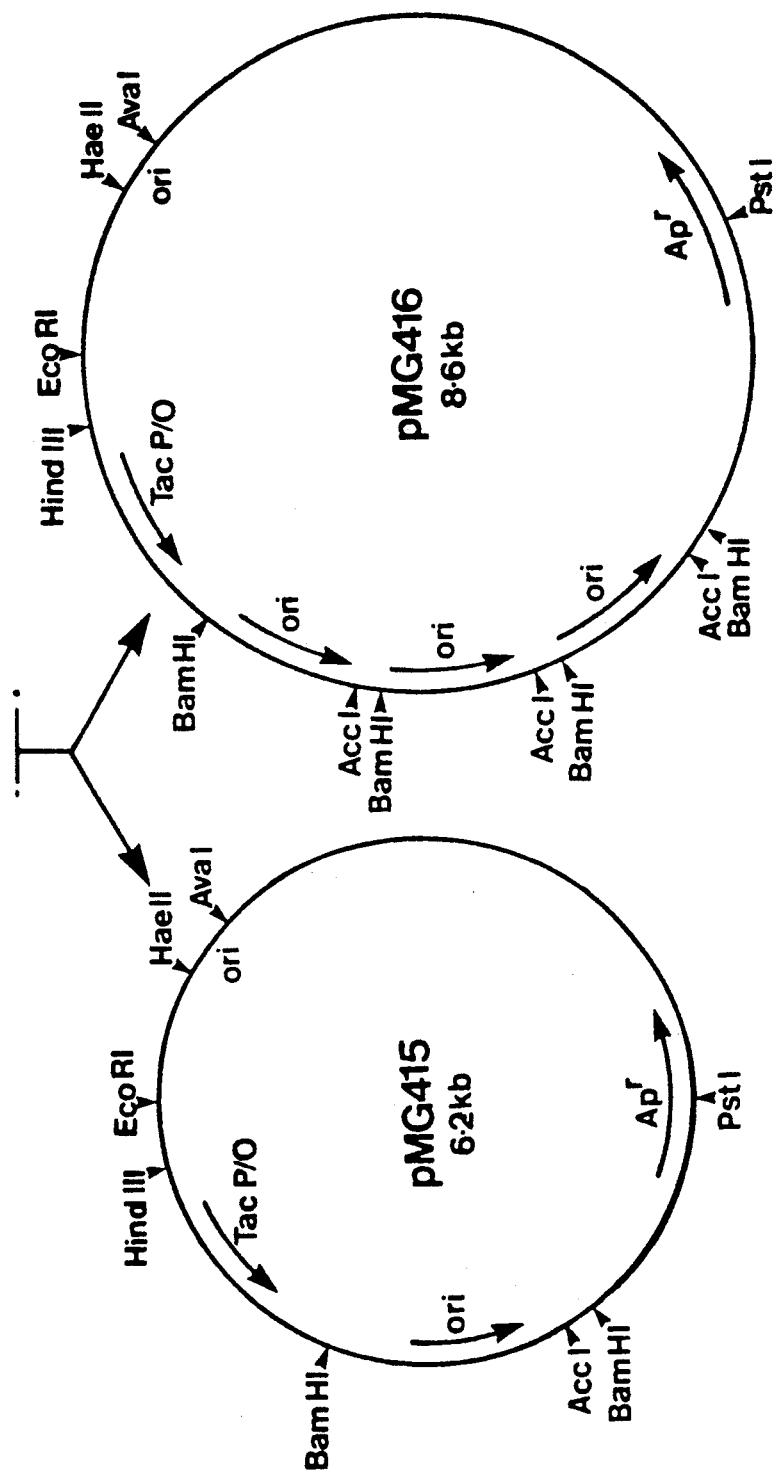
FIG. 6 (iii)

DNA VECTORS AND THEIR USE IN RECOMBINANT DNA TECHNOLOGY

This is a continuation of application Ser. No. 07/142,281, filed Dec. 30, 1987, which was abandoned upon the filing hereof, which in turn, is a continuation of Ser. No. 06/676,392, filed Nov. 20, 1984, abandoned.

FIELD OF THE INVENTION

This invention relates to DNA vectors, their production and their use in recombinant DNA technology. The invention also relates to the control of replication of DNA vectors in the cells of host organisms, and to the production of gene products.

BACKGROUND OF THE INVENTION

DNA vectors, such as plasmids, are normally circular, extrachromosomal DNA molecules which replicate autonomously within the cells of host organisms. The cells of many unicellular organisms, including some bacteria, contain naturally-occurring wild-type plasmids which contribute various functions to the host cells such as antibiotic resistance and fertility. These wild-type plasmids and derivatives of them are the basic tools of recombinant DNA technology, providing vehicles for the transformation of the cells of host organisms with foreign DNA sequences which code for production, within the transformed cells, of corresponding foreign polypeptide and protein products. Thus, in recombinant DNA techniques, plasmids are cut open at specific sites using restriction enzymes and recombined in vitro with additional DNA sequences including genes coding for desired foreign products, to give recombinant plasmids which may be used to transform appropriate host cells.

These recombinant plasmids, similar to the parent plasmids from which they are derived, are capable of autonomous replication within host cells, and on replication reproduce not only the DNA sequences of the parent plasmid but also the inserted additional DNA sequences, including the foreign genes. During protein synthesis, transcription and translation of the DNA sequences of the recombinant plasmids carried within transformed host cells give rise inter alia to the synthesis of foreign products corresponding to the inserted foreign genes.

One factor which affects the yield of synthesised foreign product is the number of copies of the foreign gene which are present within the transformed cells, i.e. the copy number at which the recombinant plasmid is maintained within the host cells, this being defined normally as the number of copies of the plasmid per host genome. Generally speaking, the higher the copy number of the recombinant plasmid the greater is the yield of foreign product. Both low copy number plasmids, usually maintained within host cells at about 1–10 copies per genome, and high copy number plasmids, usually maintained at from 11 up to several hundred copies per genome, are known. The copy number of a given wild-type replicon is controlled by DNA sequences surrounding and including a DNA sequence which defines the origin of replication. Thus hereinafter we refer to high copy number and low copy number origins of replication.

High copy number plasmids have been used in recombinant systems with a view to obtaining good yields of foreign products. This can lead to undesirable results, however, since many such high copy number plasmids tend not to be maintained stably within transformed cells and may be lost from the cells before they can be grown to sufficient levels to permit bulk production of foreign products. For example, the foreign product may inhibit propagation of the transformed cells or the high copy number plasmids themselves may be inherently unstable.

It is known that the copy numbers of some plasmids can be amplified above normal levels by inhibition of protein synthesis; for instance, by addition of protein synthesis inhibitors such as chloramphenicol to the fermentation medium. However, protein synthesis is required for production of most gene products, and therefore the inhibitor must be removed before synthesis of foreign gene products can take place. The removal of inhibitor requires complicated manipulations and is not always possible.

Various other solutions have been proposed to overcome the problem of stable maintenance of high copy number plasmids in host cells. For example, in UK Patent Specification No. 1,557,774 it has been proposed to use mutant plasmids having a temperature-dependent plasmid copy number pattern such that the plasmid shows a controlled constant plasmid copy number when host bacteria carrying the plasmid are cultivated at one temperature, but an altered plasmid copy number pattern, allowing a much higher or totally uncontrolled copy number, when the host bacteria carrying the plasmid are grown at a different temperature. Thus cells may be propagated to desired production size culture at one temperature at which the plasmid replicates at low copy number and at which its gene products do not significantly inhibit cell growth. The temperature may then be altered, greatly increasing the plasmid copy number and also the corresponding production of gene products. The introduction of copy number temperature dependence in such mutant plasmids, however, may introduce a source of instability into the plasmid, and it is likely that these mutant plasmids may be unstable or subject to loss when cells carrying them are propagated over a prolonged period of time.

The replication of plasmids is controlled by nucleotide sequences contained within the overall DNA sequence of the plasmid. These sequences include a sequence defining the origin of replication at which DNA replication is initiated and often also associated sequences which control the initiation of replication at the origin and the copy number at which the plasmid is maintained. For example, certain plasmids, of which ColE1 is a typical example, have plasmid replication systems having a number of features in common. These systems comprise a DNA sequence defining an origin of replication and upstream thereof a DNA sequence coding for transcription, in opposing directions, of two RNA species, RNAII and RNAI. The RNAII species provides and RNA primer which forms a complex at or near the origin from which DNA synthesis is initiated; the RNAI species interferes with the formation of this initiation complex. Transcription of the two RNA species is controlled by separate promoter sequences associated with the DNA sequences which code for their transcription. In addition there is a small polypeptide (the rop protein) which is believed to interact with the promoter for RNAII; this polypeptide is not essential for replication and its role is unclear. The origin of replication, the RNA coding sequences and associated promoters together provide an internally self-regulated system which controls the replication incompatibility and the copy number of these plasmids. Certain other plasmids, exemplified by RI and some Staphyloccocal plasmids, also control replication initiation at the transcriptional level, but by a messenger RNA species whose product provides an initiation factor, probably a polypeptide, which is involved in DNA replication.

It is an object of the present invention to provide new DNA vectors which have controllable copy number patterns and thereby overcome problems associated with stable maintenance of vectors which replicate at high copy number only, which new vectors will not be subject to the potential instability of previously described mutant plasmids which have temperature-dependent copy number patterns, and which, furthermore, will have the advantage that their copy number can be controlled by agents other than temperature, e.g. metabolite concentration.

Accordingly, in a first aspect the invention provides a DNA vector comprising two replication systems; a first origin of replication resulting in a low copy number and stable inheritance of the vector and a second, high copy number origin of replication at which replication is directly controllable as the result of replacement or alteration by DNA manipulation of the natural vector sequence(s) which control replication at said origin.

By means of the invention, when host cells carrying the vector are propagated under a first set of conditions, replication takes place mainly, and preferably exclusively, from the low copy number origin, and when the cells are propagated under a different set of conditions, replication takes place at high copy number at the second origin as well and the production of large amounts of foreign gene products encoded by the vector is induced.

In a second aspect the invention provides a DNA vector containing a replication system comprising an origin of replication and an associated DNA sequence encoding and RNA species which provides a primer or initiation factor (e.g. a polypeptide) which initiates DNA replication by formation of a complex at or near the origin of replication, in which transcription of said RNA species is directly controllable such that, when host cells carrying the vector are propagated under selected conditions, replication takes place at high copy number from the origin and the production of large amounts of foreign gene products encoded by the vector is initiated.

Preferably the second replication system of the first aspect of the invention is a replication system as specified in the second aspect of the invention.

The invention also includes a method for the preparation of a vector according to the first aspect, comprising including in the DNA sequence coding for the second replication system a DNA sequence which permits direct control of replication at the second origin.

Methods for the preparation of vectors according to the first aspect of the invention suitably comprise ligating a first DNA sequence coding for the replication system comprising the first origin with a second DNA sequence coding for the secondary replication system. The DNA sequence which permits direct control of replication at the second origin may be incorporated into the second DNA sequence either before or after ligation with the first DNA sequence. Thus the invention further provides methods for the preparation of vectors according to the second aspect of the invention, comprising including in the second DNA sequence a DNA sequence which permits control of replication at the second origin by controlling transcription of the RNA species.

The invention further includes a process for the production of a polypeptide, protein or other gene product which comprises transforming host cells with a vector according to the first aspect of the invention, in which said vector contains a gene sequence coding for production of said polypeptide, protein or other gene product, propagating said transformed cells under a first set of conditions at which replication takes place at low copy number mainly, and preferably exclusively, from the first origin, and then propagating said transformed cells under a second set of conditions at which replication takes place at high copy number also (or exclusively) from the second origin and the expression of said polypeptide, protein or other gene product is induced.

By means of the process of the invention, transformed cells are propagated to give the large scale cultures required for economic production of polypeptide, protein or other products under conditions where the vector replicates at low copy number and the instability problems associated with high copy number vectors are avoided, followed by propagation under different conditions where the vector replicates at high copy number with concomitant high yield of polypeptide, protein or other products.

In particular it has been found, when the expression of the gene product is under the control of a promoter which is regulated by cytoplasmic levels of a repressor, that the increase in vector copy number leads to outstripping of the repressor control and high level expression of the gene product. This is so even in the case when the synthesis of the repressor is autoregulated, e.g. when the promoter/repressor system is that of the tryptophan operon.

The control systems which are used to control the copy number of the vectors of the invention may comprise any of the control systems which are known for controlling replication (and/or expression) in recombinant DNA technology. In particular, the copy number of the controllable origin of replication may be controlled by temperature or one or more metabolites or metabolite analogues. Examples of metabolite-dependent systems which may be used include: tryptophan, lactose, galactose, arabinose or any other metabolite or metabolite analogue, the presence, removal or further metabolism of which can be used to achieve transcription from a given promoter.

The controllable replication system used in the vectors of the invention may be derived from high copy number cloning vectors, such as ColE1-like plasmids, e.g. pAT153, NTP1, CloDF13, RSF1030 or P15A, which have copy number control systems which involve transcription of RNAII or a similar RNA species which provides a primer which initiates DNA replication by formation of a complex at or near the origin or replication. In addition other plasmid replication origins whose replication is controlled by an mRNA species and/or its product(s) may provide the controllable replication systems used in the vectors of the invention. Such replication origins may be obtained from Gram negative bacterial species and are exemplified by R1, R6, R100, RP4, or Gram positive bacterial species, which are exemplified by pUB100, pC194 and certain other Staphylococcal plasmids. Furthermore, bacteriophage origins may be used for secondary controllable origin, e.g. those from λ, T3, T4, T7, M13,φX174, SPP1, SPO2 etc.

In an important embodiment of the invention, the controllable replication systems may be prepared from such high copy number cloning vectors by replacement of the natural promoter, which promotes transcription of the RNA species, by a controllable promoter, such as the $P_L$ promoter, $P_R$ promoter, $P_{re}$ promoter, $P'_R$ promoter, T7late promoters, trp promoter, tac promoter, lac promoter, gal promoter, ara promoter or recA promoter (the origin of replication in such a system is termed a "hybrid origin"). Alternatively the natural promoter may be used and transcription of the RNA species made controllable by incorporating a regulating function, such as an operator sequence, e.g. the lac operator or $O_L$ or $O_R$ operators of phage lambda, into the replication systems.

The plasmids pMG9 (containing an Xho I linker DNA sequence inserted as described by K. Tatchell et al, Cell, Vol 27, pages 25-35, November 1981 (Part 2)) provides a convenient starting material for preparation of a controllable replication system based on the ColE1 replication origin. This plasmid has a unique Xho I restriction site, close to the start of the sequence coding for transcription of the RNAII species, which we have found may be used for insertion of operator and controllable promoter sequences, e.g. $\lambda P_L$, to give a directly controllable replication system.

The replication system comprising the first origin of replication may be obtained from any suitable low copy number plasmid. For example, a replication system comprising the pSC101 origin may be used, and the plasmid pHSG415 (T. Hashimoto-Gotoh et al, Gene, 16 (1981) pages 227-235) provides a convenient source for such a replication system. It will be appreciated that pHSG415 has a temperature sensitive replication origin, but that this origin may be replaced by its wild-type temperature-stable counterpart from pSC101. pHSG415, however, provided a convenient, temperature sensitive replication origin for use in the examples hereinafter described.

Controllable functions may be incorporated into high copy number replication systems, high copy number and low copy number replication systems may be ligated, and foreign genes may be incorporated into the vectors to produce vectors according to the invention using techniques which are known and understood by workers skilled in the recombinant DNA art. The resultant vectors may then be used to transform suitable host cells using standard procedures to produce foreign polypeptide, protein and other products.

The host cells may comprise eucaryotic cells, including yeast cells e.g. S. cerevisae, or, more usually, bacterial cells, of species such as B. subtilis or, especially, E. coli.

The invention is further described by way of illustration only in the following Examples, Examples 1-7. These Examples relate to the construction of specific dual origin plasmids according to the invention, and to studies of copy number control, heterologous gene expression and stability of these plasmids. It will be appreciated that the invention is not limited to the specific plasmids and methods described.

These Examples refer to the accompanying diagrams in which:

FIG. 1 shows plasmid restriction maps and indicates the DNA manipulations which were used to prepare a dual origin plasmid according to the invention, pMG411;

FIG. 2 is an agarose gel of DNA isolated from cultures of a pMG411 transformant of E. coli QY7 taken at hourly intervals following a temperature shift from 30° C. to 42° C. (lanes 1-7, hours 0-6);

Figure 9:
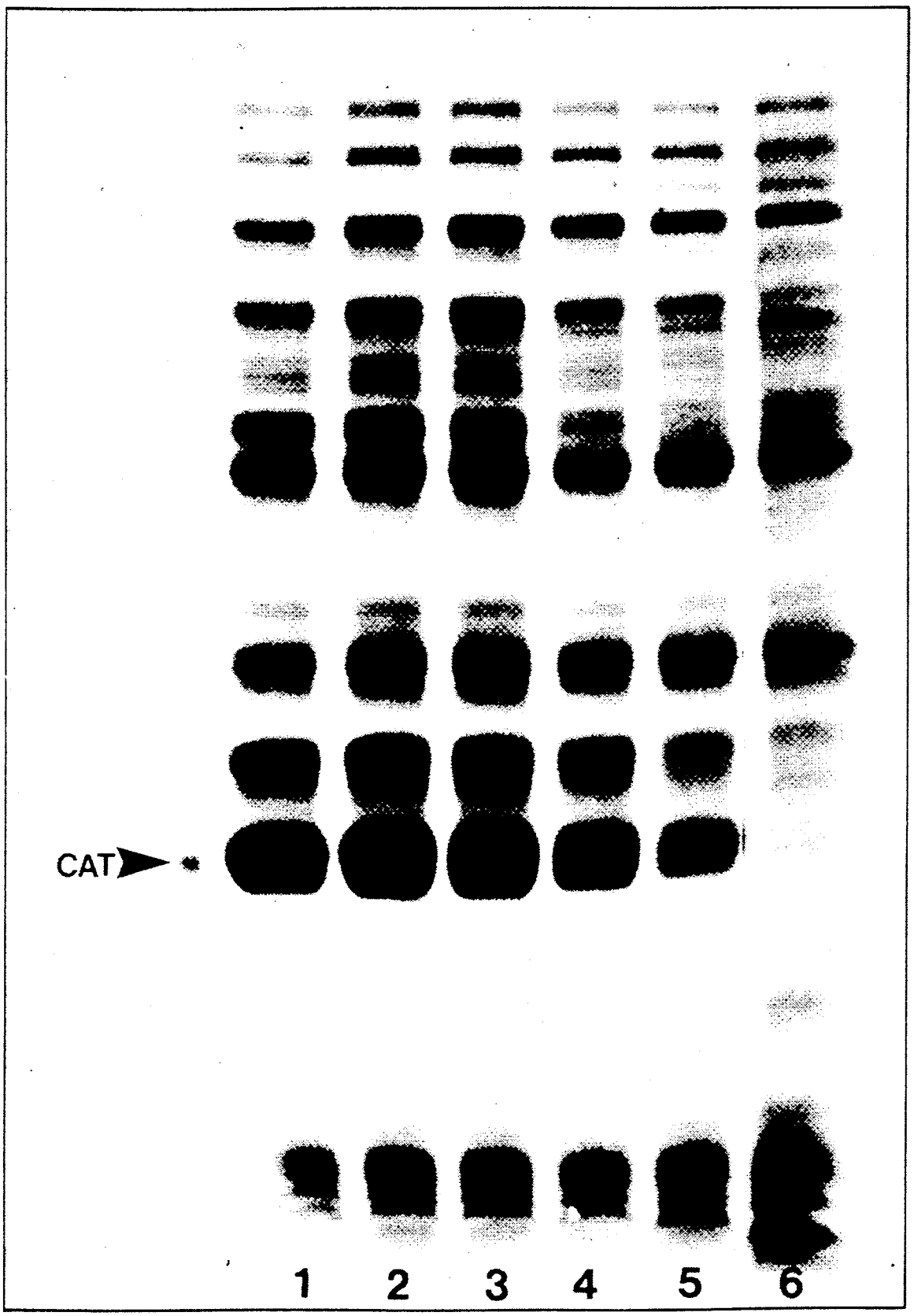

FIG. 8 is a graph showing increase in plasmid copy number and chloramphenicol acetyltransferase activity for cultures of E. coli E103(S) transformed by pMG169 after temperature shock treatment, and FIG. 9 is a 10% polyacrylamide gel of protein from total cell extracts of cultures of pMG169 transformed E. coli E103(S) at hourly intervals over a period of 5 hours after temperature shock treatment (lanes 6-1, hours 0-5).

EXAMPLE 1

Construction of a Dual-origin Plasmid with Copy Number under P1 Control (a) Construction of a Dual-origin Plasmid pMG404

Plasmid pMG15 (FIG. 1) is a derivative of RSa-12 (pBR322 replicon) which has constitutively high copy number (approximately 300 copies per chromosome) due to the insertion of a XhoI linker (CCTCGAGG) into the origin region (Table 1) (Tatchell et al, 1981). During construction of RSa-12 the rop gene was lost by spontaneous deletion extending beyond the SalI site in the tet gene, but retaining the BamHI site. The position of the XhoI linker was determined by inserting the 1.1 kb XhoI-BamHI DNA fragment of pMG15 into bacteriophage M13mp8 and DNA sequencing from the XhoI site by the method of Sanger et al, (1977).

Figures 1, 1I:
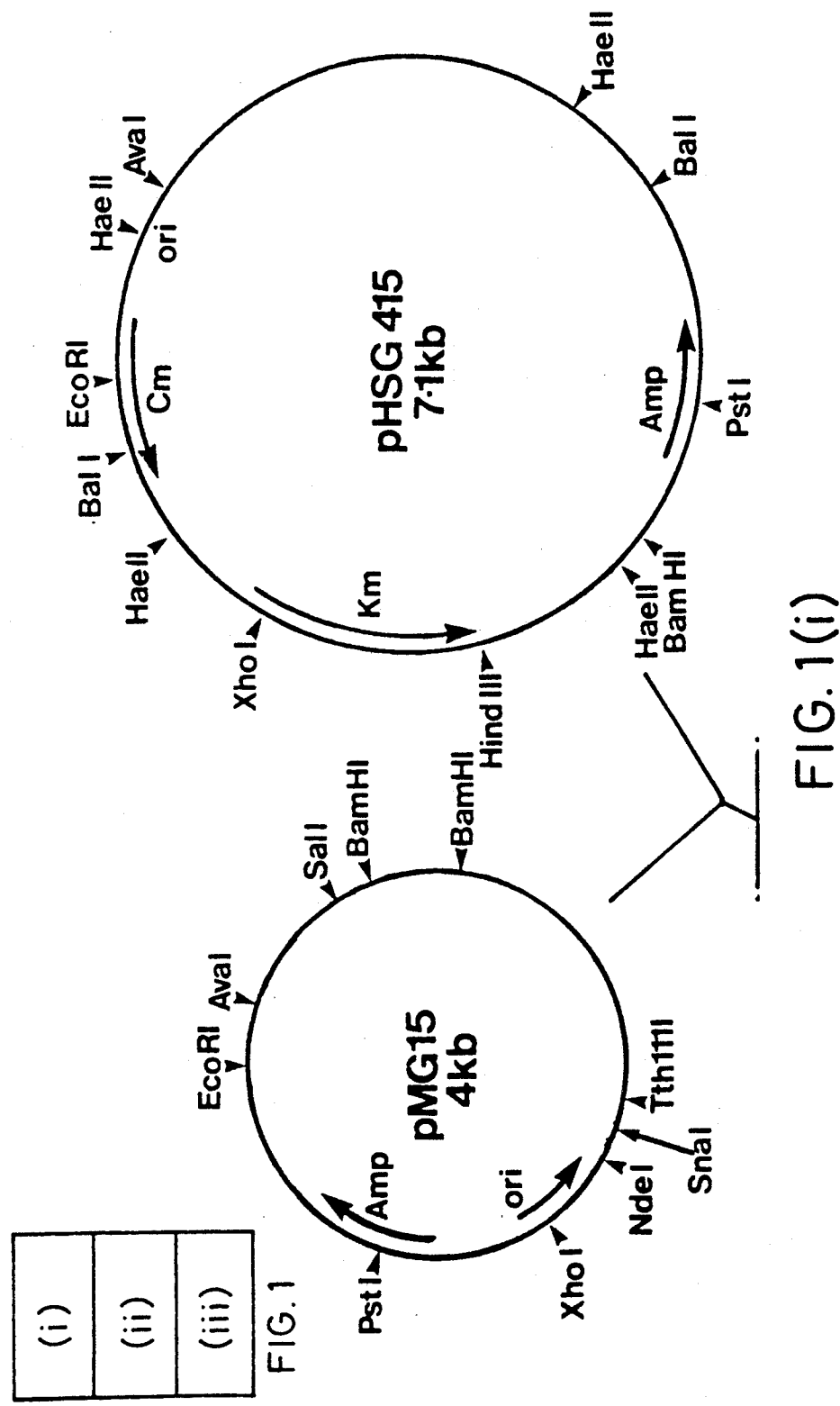
Figure 1:
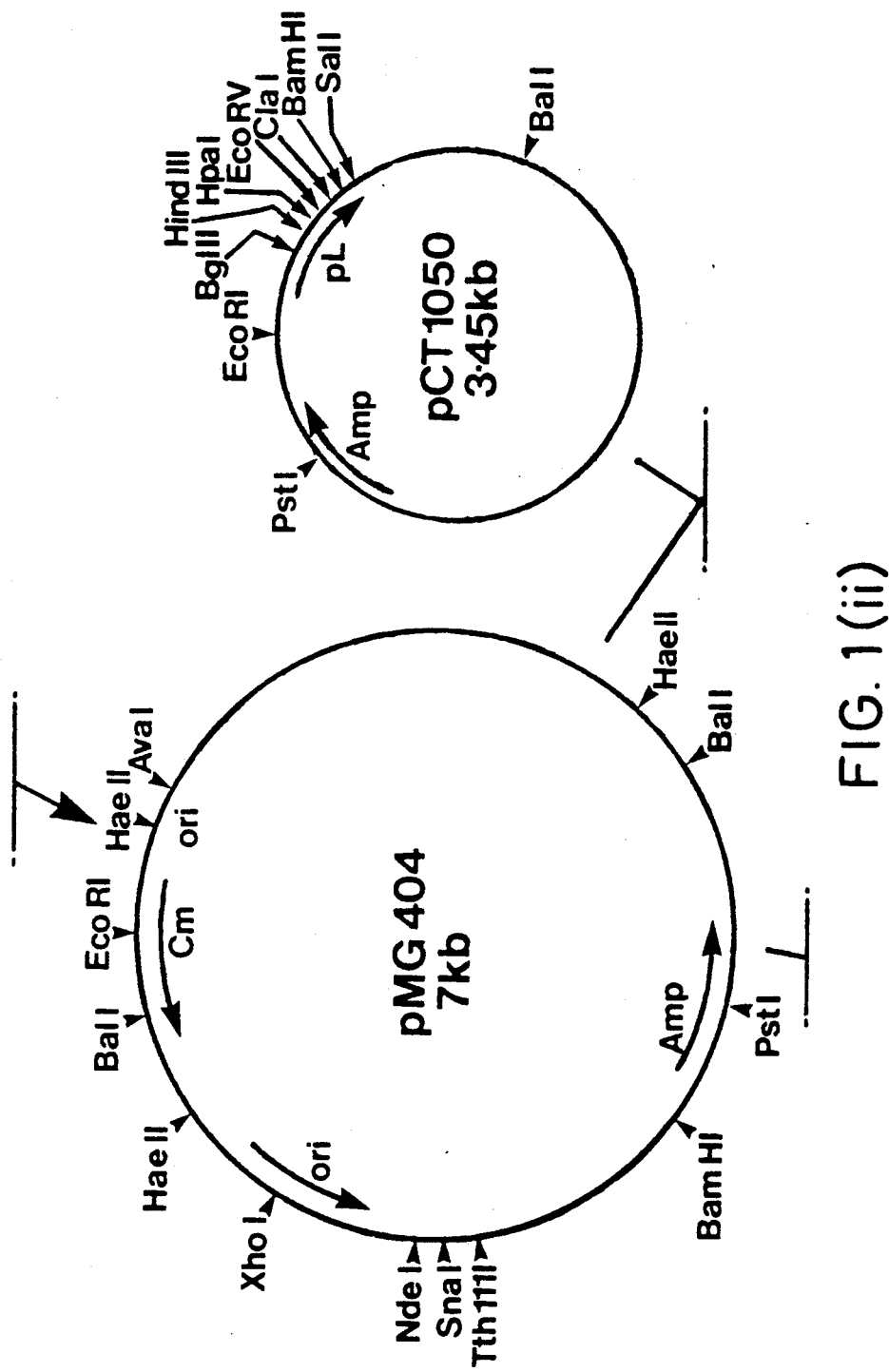

Insertion of the linker was at a point 30 bases downstream of the transcriptional start of RNAII (Table 1). This XhoI linker provided a unique cleavage site close to the 5' end of the RNAII transcript, such that the 1.1 kb XhoI-BamHI fragment isolated from pMG15 carried a promoterless RNAII sequence (FIG. 1). To determine if this sequence could function as a primer of DNA replication when coupled to another promoter, the 1.1 kb fragment was inserted downstream of the Dm resistance gene ($Km^R$) promoter of plasmid pHSG415 (Hashimoto-Gotoh et al, 1981) (FIG. 1). pHSG415 is a stable low copy number $Ap^R Km^R Cm^R$ plasmid whose replication origin is derived from pSC101; this plasmid replicates at 30° C. but not at 42° C.

TABLE 1
Site of Insertion of XhoI Linker near the Origin

WILD TYPE SEQUENCE

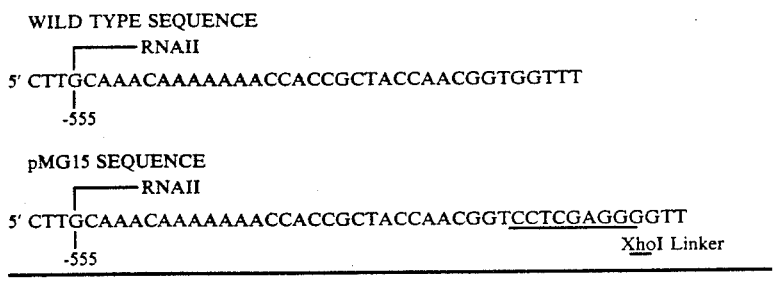

pMG15 SEQUENCE

Conditions for restriction enzyme digestions, DNA ligations, and agarose gel electrophoresis were as described in Maniatis et al (1982). Insertion of the XhoI-BamHI fragment from pMG15, coupling the promoterless RNAII sequence to the $Km^R$ promoter, gave the dual origin plasmid pMG404 (FIG. 1). Analysis of the plasmid pMG404 by restriction enzyme digestion verified its structure (results not shown), and plasmid DNA yields demonstrated that its copy number was considerably higher than that of pHSG415. In addition, pMG404 was maintained in bacteria at 42° C. whereas pHSG415 was lost due to its inability to replicate at that temperature. It was concluded that the hybrid 'ColE1 origin' was functioning in pMG404, demonstrating that the $Km^R$ gene promoter could substitute for the RNAII promoter.

Confirmation of the functioning of the hybrid origin was obtained by digesting pMG404 with BalI and recirculating the larger fragment containing only the hybrid origin. This generated a plasmid pMG410 which was capable of autonomous replications at both 30° C. and 42° C., demonstrating that the hybrid origin was functional.

(b) Construction of Dual-origin pMG411

Plasmid pMG404 has two origins or replication: the low copy number origin of pSC101 and the 'ColE1' hybrid origin. The pSC101 origin should ensure stable replication of the plasmid at 30° C. (Hashimoto-Gotoh et al, 1981), allowing the construction of derivatives with the 'ColE1' hybrid origin driven by a controllable promoter. A 0.5 kb SalI-EcoR1 DNA fragment carrying the P1 promoter of bacteriophage λ was isolated from the plasmid pCT1050 (FIG. 1) and ligated to the 5.5 kb EcoR1-XhoI fragment from pMG404. The ligation mixture was used to transform E. coli QY7 (λ cI857 defective lysogen) and DH1 at 30° C., and the $Ap^R$ transformants screened for $Cm^S$ clones. One of these, pMG411 was chosen for further study (FIG. 1). Plasmid pMG411 transformants of DH1 and QY7 grew well under selective conditions and copy number determinations were made at a variety of growth temperatures.

(c) Copy Number Measurements of pMG411

Plasmid copy number as determined by two methods. One depended upon the separation of chromosomal and supercoiled DNA by caesium chloride centrifugation. The second method depended upon the separation of chromosomal and plasmid DNA by agarose gel electrophoresis. Cells were grown overnight in L-broth containing ampicillin, and diluted one hundred fold into minimal M9 salts medium containing ampicillin. At an $OD_{660}$ of 0.5, 2-deoxyadenosine (200 μg/ml) thymidine (1 μg/ml) and [$^3$H]-thymidine (4 μg Ci/ml) were added, and incubation continued for 2 hours. Cells were centrifuged, washed and resuspended in an equal volume of 50 mM tris ECl pH 7.5, 10% sucrose (w/v) and lysozyme (200 μg/ml). After incubation for 10 minutes at 0° C., EDTA was added to a concentration of 10 mM and incubation continued for 10 minutes, and finally sarkosyl (0.4% w/v) was added. Chromosomal DNA in the lysate was sheared by 6 passages through a 19 gauge needle, and cell debris removed by centrifugation. DNA preparations were further purified by a single phenol and chloroform extraction and ethanol precipitation. This labelled DNA preparation was then used for copy number determination by either method.

For the agarose gel method, samples were electrophoresed on a 0.7% agarose gel (in 0.04 M tris acetate, 0.001 M EDTA, pH 7.9) for 12 hours at 50 V. DNA bands were visualised by staining in ethidium bromide. The chromosomal and plasmid DNA bands were cut from the gel, dissolved in saturated sodium iodide and the DNA precipitated by the addition of 10% (w/v) trichloroacetic acid (TCA). Precipitates were collected on GF/C Whatman filters, washed in 10% (w/v) TCA, ethanol and then air dried. Radioactivity was determined by counting in a liquid scintillation counter.

For copy number determinations by caesium chloride centrifugation DNA samples were centrifuged to equilibrium in caesium chloride-ethidium bromide in a Beckman TI50 rotor at 48,000 rpm for 24 hours. The gradients were fractionated, and the fractions precipitated with TCA onto GF/C Whatman filters, washed and processed as described above.

Plasmid copy numbers were determined from pMG15, pAT153 and pMG411 at 30° C., 37° C. and 42° C. and the results obtained are given in Table 2.

TABLE 2
Variation of Plasmid Copy Number with Temperature

| Plasmid | Bacterial Strain (growth temperature) | Percentage of total DNA | Copies of Chromosome |
|---|---|---|---|
| pMG15 | HB101 (37° C.) | 33 | 309 |
| pAT153 | HB101 (37° C.) | 5.8 | 59 |
| pMG411 | QY7 (30° C.) | 0.7 | 4 |
| pMG411 | QY7 (37° C.) | 13.5 | 78 |
| pMG411 | QY7 (42° C.) | 24.8 | 143 |

Measurements of pMG411 copy number in strain QY7 (λ lysogen) at various temperatures demonstrated that the λ repressor controls pMG411 copy number. After growth at 30° C., copy number was estimated at 4 per chromosone, whilst at 37° C. it had increased to 78 and at 42° C. it has increased to 143 per chromosome (Table 2).

Figure 2:
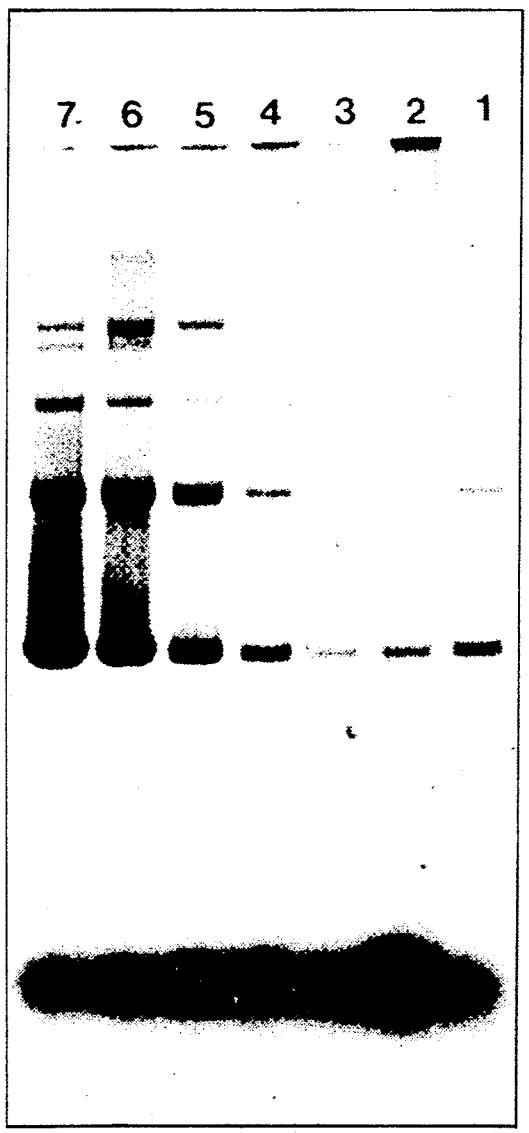

To demonstrate that the hybrid 'ColE1' origin in pMG411 could be switched on by inactivating the λ repressor, a transformant of QY7 was grown at 30° C., and then the temperature raised to 42° C. during exponential growth. The plasmid copy number increase was followed by agarose gel analysis of DNA isolated from 1 ml cultures (FIG. 2). Samples were taken at 1 hour intervals over a period of 7 hours. As predicted, an increase in pMG411 copy number was observed over the 7 hour period.

EXAMPLE 2

Construction of Dual Origin Plasmids with Inducible Copy Number under Pr Control (a) Construction of Dual Origin Plasmids pMG159 and pMG165

Plasmid pMG411 has two origins of replication, the low copy number origin of pSC101, and the P1-driven ColE1 origin. Since the repressor gene, $cI_{857}$ is required for copy number control this limits the use of pMG411 to lysogenic bacterial strains. To overcome this constraint, a dual-origin plasmid carrying the $cI_{857}$ gene was constructed.

Figure 3I:
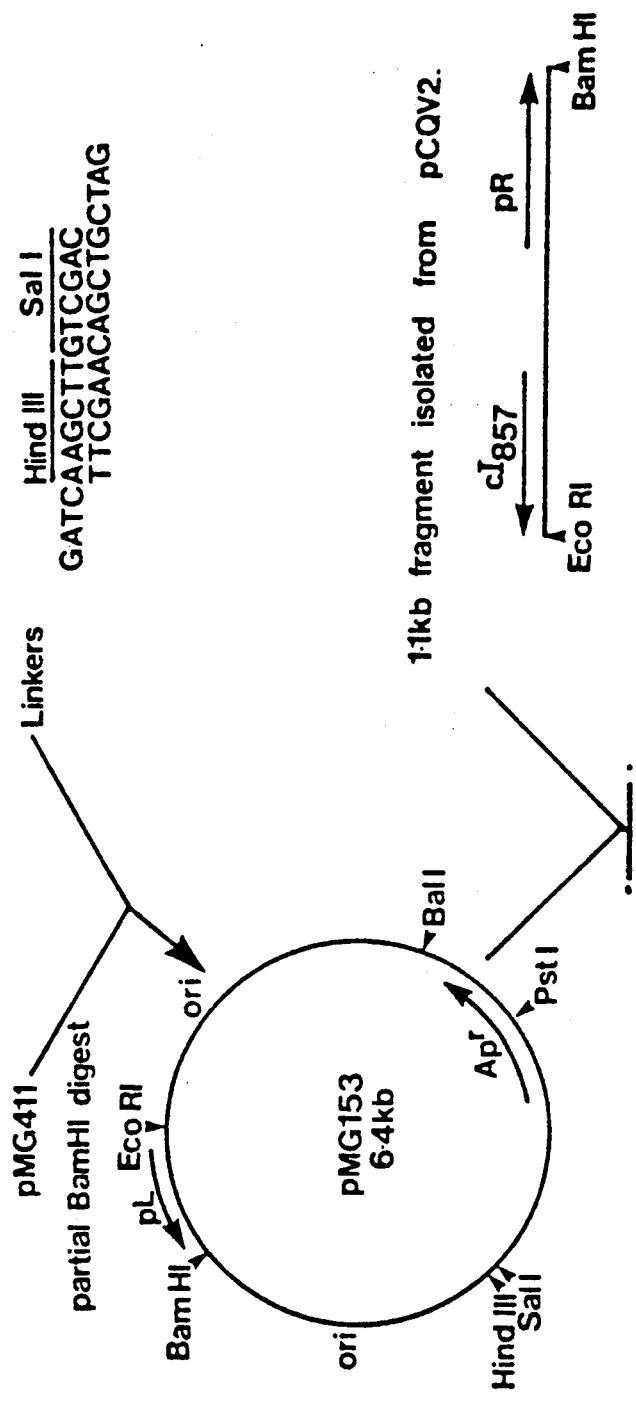
FIG. 3 shows plasmid restriction maps and indicates the DNA manipulations used to prepare two further dual origin plasmids according to the invention, pMG159 and pMG165.
Figure 3:
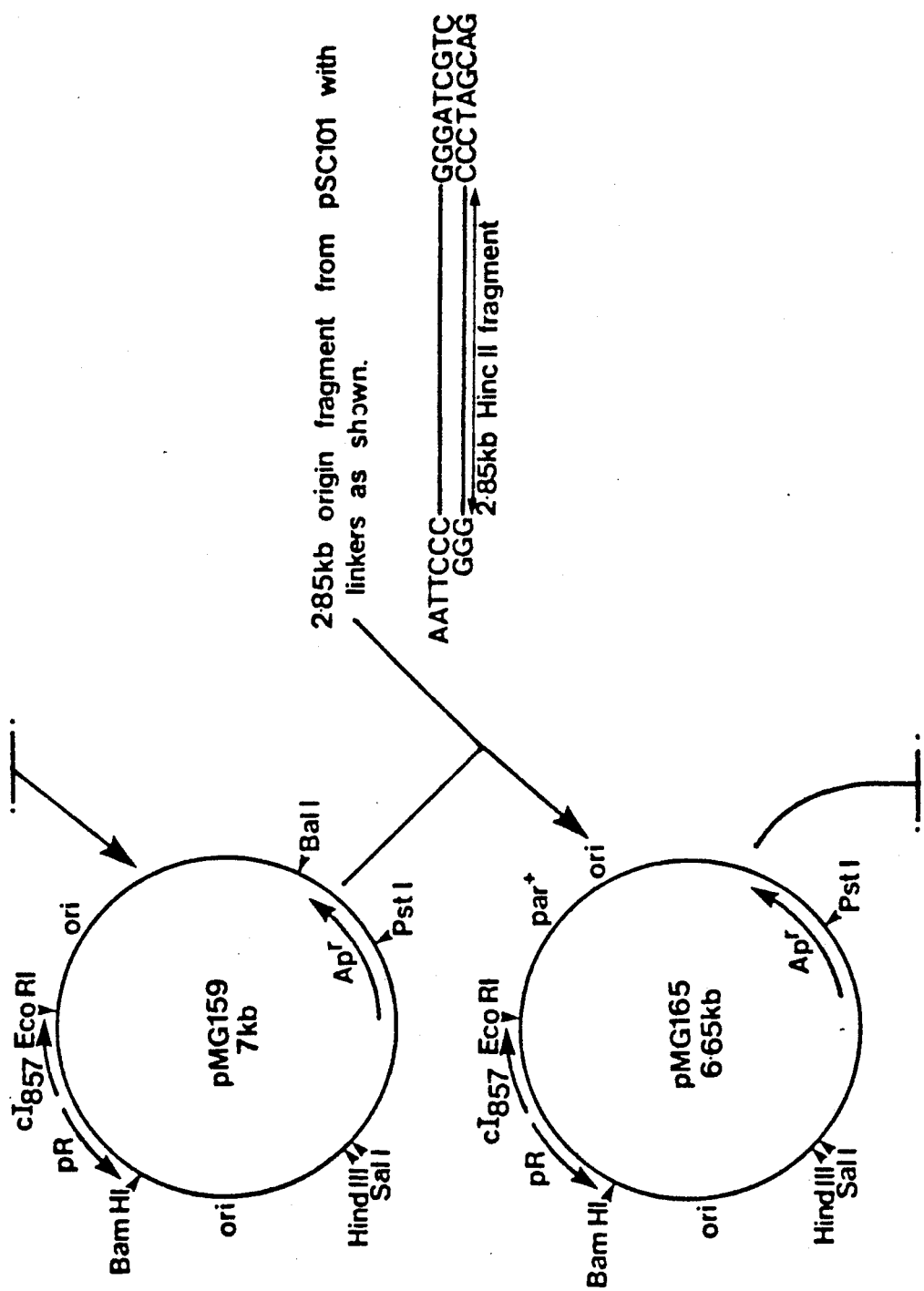

Firstly, to facilitate subsequent cloning of foreign genes an oligonucleotide comprising a SalI and HindIII restriction site was inserted into the BamHI site immediately downstream of the hybrid origin in pMG411; this gave pMG153 (FIG. 3). The 5.9 kb EcoR1-BamHI fragment of pMG153 was purified and ligated to a 1.1 kb EcoR$^1$-BamHI fragment of pCQV2 (Queen, 1983), to give pMG159. The EcoR1-BamHI fragment of pCQV2 carries both Pr and the $cI_{557}$ gene, and on insertion into pMG153, replaces the P1 containing fragment, fusing the ColE1 origin RNAII sequence to Pr. Note that the repressor gene is transcribed away from the origin (FIG. 3). To increase plasmid stability (see below) when the dual-origin vectors are maintained at 30° C., the pSC101 2.85 kb HincII fragment carrying the origin or replication, replication protein and par sequence, was introduced into pMG159, by replacing the 3.25 kb EcoR1-BalI fragment with the pSC101 HincII fragment with an EcoR1 linker at one end. This gave pMG165 (FIG. 3).

(b) Copy Number Control of Pr Driven Dual Origin Plasmids

To demonstrate that the 'ColE1' hybrid origin driven by Pr was controlled by the temperature sensitive repressor expressed from the cloned $cI_{857}$ gene, pMG159 and pMG165 were transformed into *E. coli* E103(S). Copy number determinations at 30° C. were made as previously described from $^3$H-thymidine labelled cells (Table 3). Copy number induction after temperature shift to 42° C. was followed by agarose gel electrophoresis. To quantitate the copy number change and kinetics of induction in L-broth, a 'spot' hybridisation method was used.

TABLE 3

Variation of Plasmid Copy Number with Temperature

| Plasmid | Bacterial Strain (growth temperature) | Copies per Chromosome |
|---|---|---|
| pMG159 | E103(S) (30° C.) | 3–4 |
| pMG165 | E103(S) (30° C.) | 3–4 |
| pMG159 | E103(S) (42° C.) | ~320 |
| pMG165 | E103(S) (42° C.) | ~248 |

For the 'spot' hybridisation method $^{32}$P-labelled probe DNA was prepared by nick translation (Maniatis et al, 1982). DNA samples were prepared by the alkaline lysis method (Ish-Horowitz and Burke, 1981) from 1 ml of culture taken at various times after the temperature shift. Samples of the DNA preparations were treated with RNase at 37° C. for 5 minutes, followed by incubation with restriction enzyme BamHI for 30 minutes, and heat denaturation at 100° C. for 3 minutes. Varying amounts of the digested DNA preparations were spotted onto nitrocellulose filters, which were then dried at 70° C., and subsequently hybridised overnight (15 hours) with the denatured probe DNA at 37° C. in 2xSSC/50% formamide. Filters were then washed twice in 2xSSC/50% formamide and once in 2xSSC, and then air dried. Radioactivity was determined by counting in a liquid scintillation counter. The values obtained were corrected for cell growth during induction, and the magnitude of the copy number change over the uninduced value was determined.

Both pMG159 and pMG165 showed a rapid copy number induction following a temperature shift to 42° C. and continued incubation at 37° C. Uninduced values of 3–4 copies per chromosome rising to 90–100 copies after 2 hours induction, and up to 300–400 copies after 4–5 hours induction were obtained (FIG. 4), clearly demonstrating the control of copy number exerted by the cloned Pr promoter and $cI_{857}$ gene.

EXAMPLE 3

Figure 5:
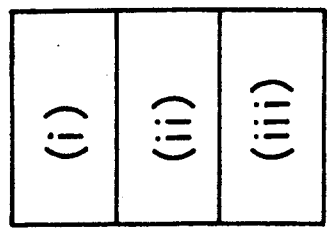
FIG. 5 shows plasmid restriction maps and indicates the DNA manipulations used to prepare a metabolite controllable dual origin vector according to the present invention, pMG427.
Figure 5I:
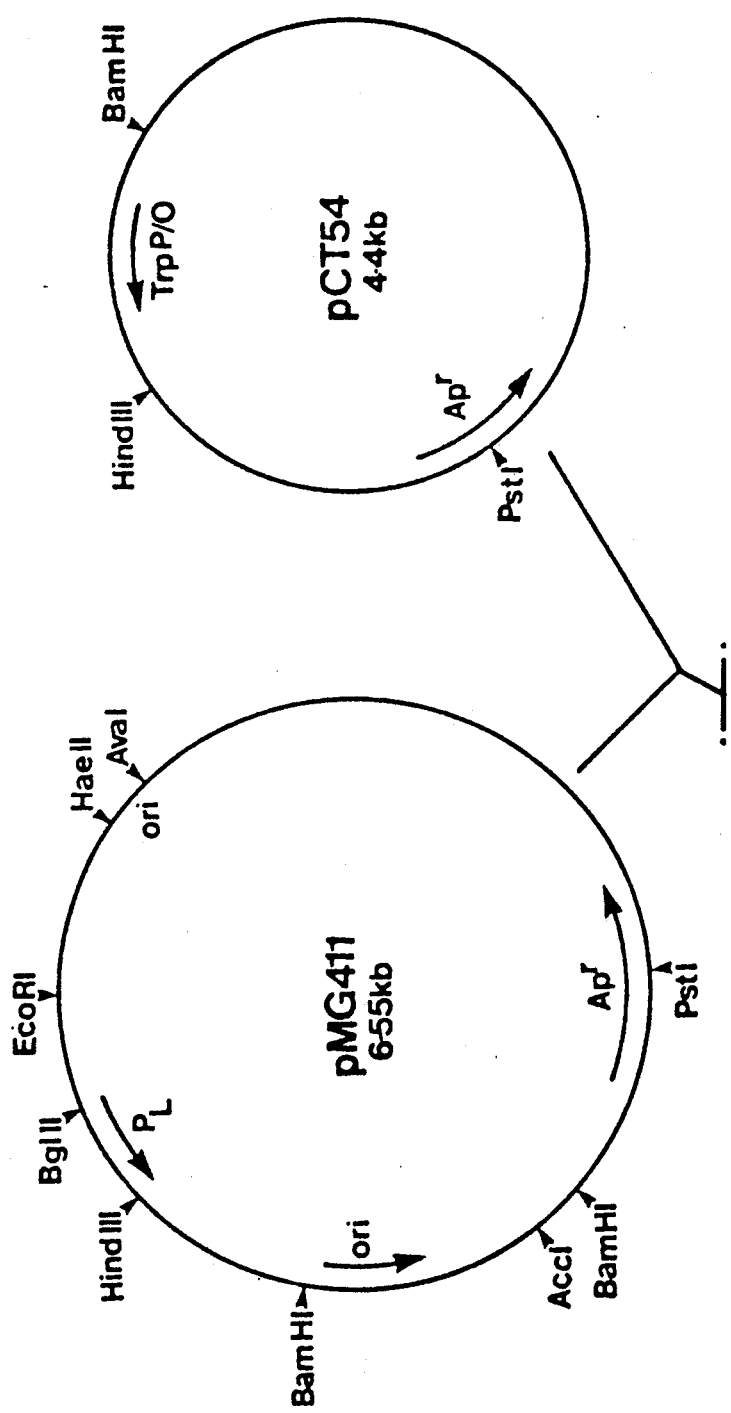
Figure 5:
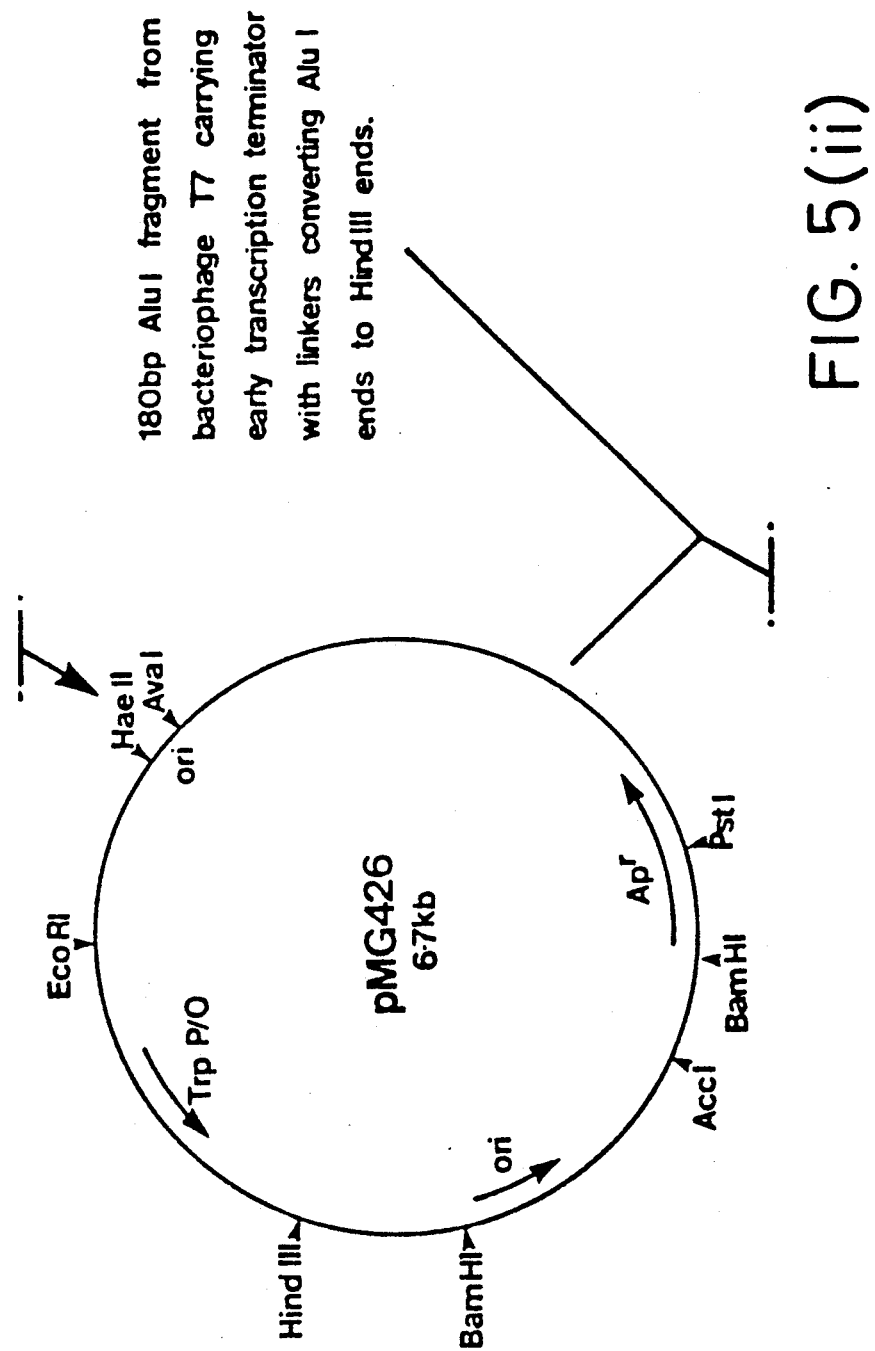

Construction of Dual Origin Plasmids with Inducible Copy Number under Ptrp Control The two above Examples of dual origin plasmids with controllable copy number, employed the use of temperature as the inducing agent, this Example describes the use of a metabolite to control copy number. The 6.2 kb HindIII-BglII fragment of pMG411 was ligated to the 0.65 kb HindIII-BamHI fragment of pCT54 (FIG. 5) using standard buffers and techniques (Maniatis et al, 1982) to give pMG426. This plasmid was unstable even under ampicillin selection and with tryptophan present in the medium (which should repress transcription from Ptrp). It was concluded that the instability was due to the inability to repress completely transcription from Ptrp, thereby giving a high copy number. To decrease transcription through the origin, a transcriptional terminator was inserted between the Ptrp and the 'ColE1' origin sequence. Such terminators reduce levels of transcription approximately 10-fold. A 180 bp AluI fragment from bacteriophage T7 DNA, carrying the early transcription terminator was ligated to DNA linkers converting the termini to HindIII recognition sites (Emtage et al 1983). This fragment was then ligated to HindIII digested pMG426 DNA to give pMG427 (FIG. 5). pMG427 was more stable than pMG426 and when transformants were grown in medium containing tryptophan (100 μg/ml) it exhibited a low copy number. When such a culture was shifted into medium lacking tryptophan, the copy number increased rapidly. This demonstrates that RNAII transcription can be controlled by the levels of metabolites or chemicals in the external medium, and that controlled copy number changes can be effected by agents other than temperature.

EXAMPLE 4

Figure 6:
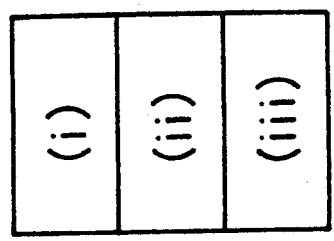
FIG. 6 shows plasmid restriction maps and indicates the DNA manipulations used to prepare two further metabolite controllable dual origin vectors according to the invention, pMG415 and pMG416.
Figure 6I:
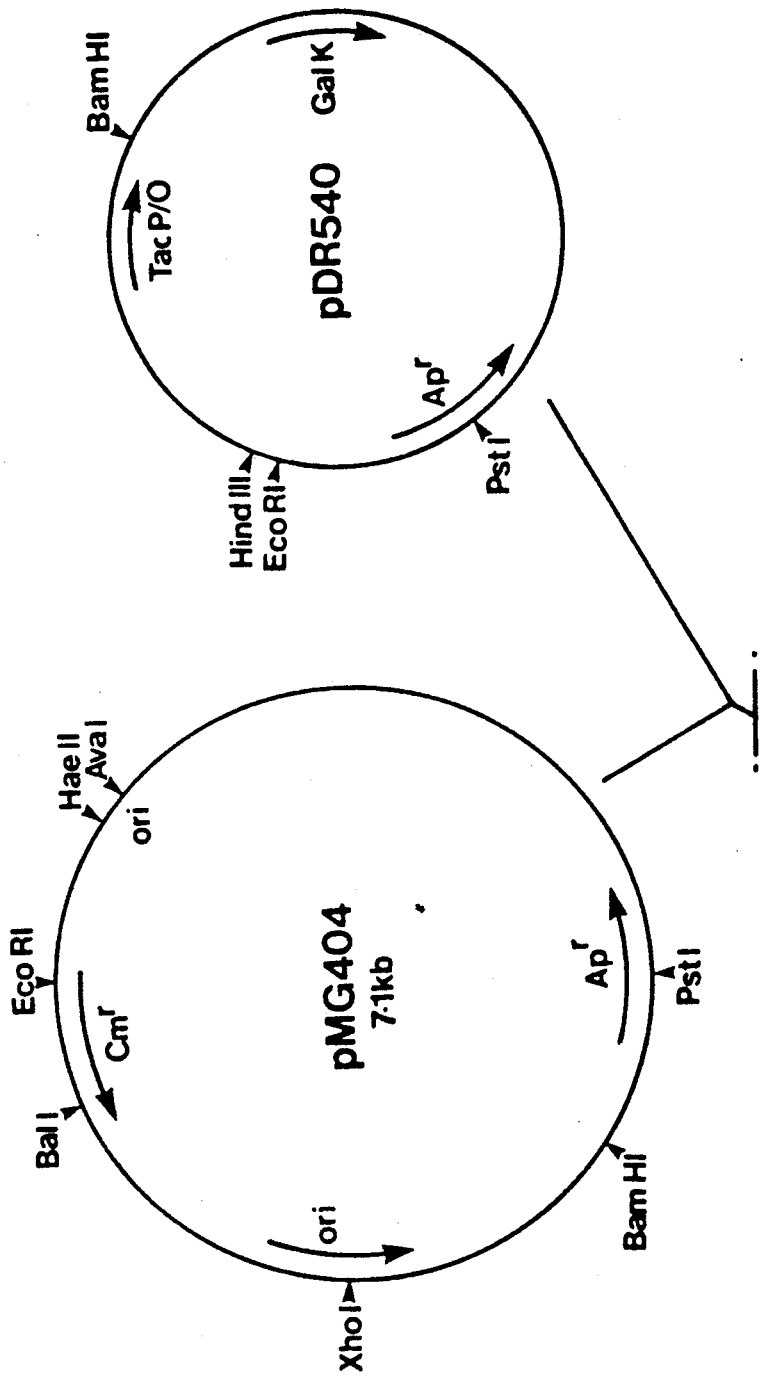
Figure 6:
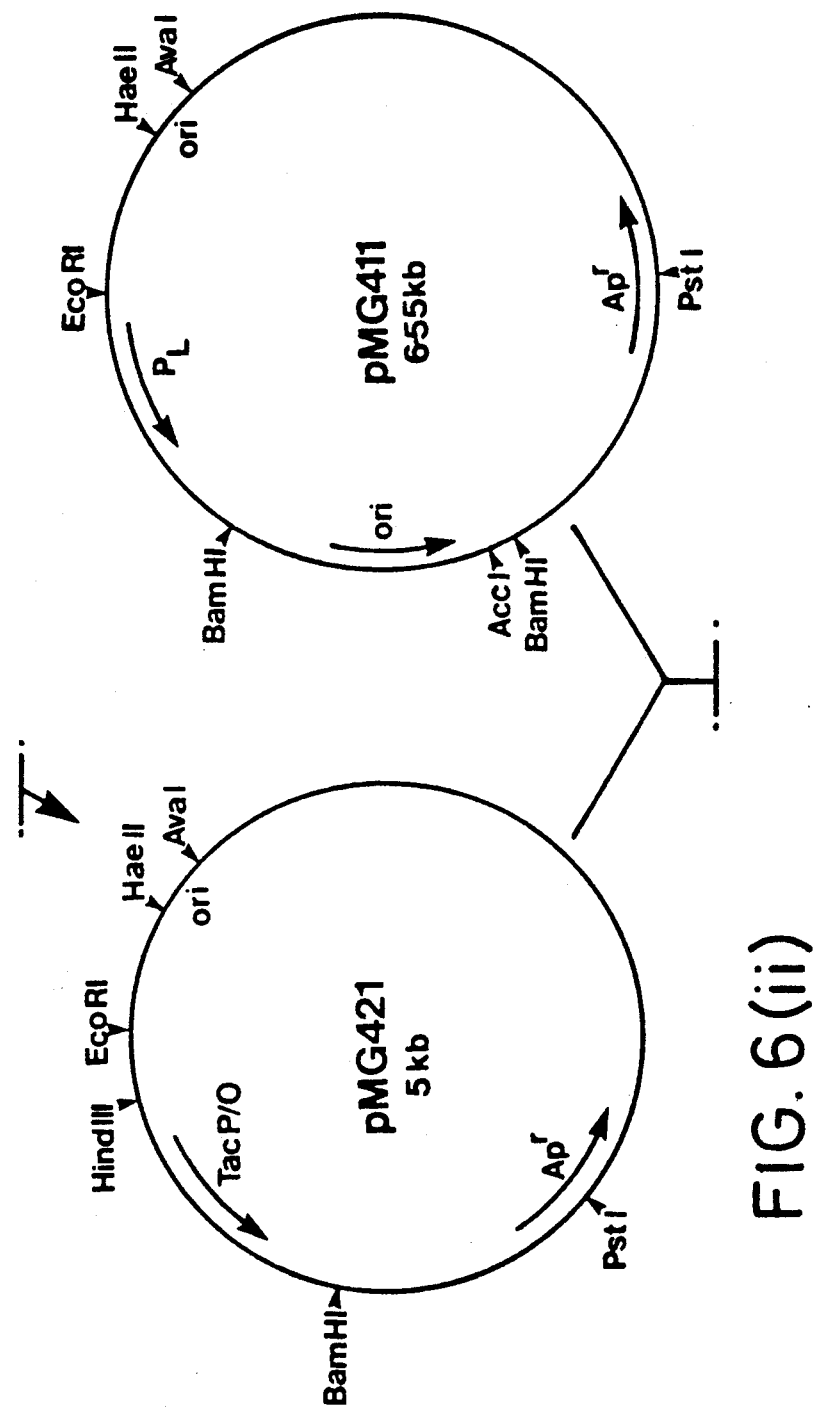

Construction of Dual Origin Plasmids with Inducible Copy Number Under Control of the 'tac' Promoter In this Example a vector was constructed where the RNAIII promoter was replaced by the tac promoter (Ptac) (Russell and Bennet 1982), such that copy number was controlled by the addition or removal of lactose or a lactose analogue. A 121 bp BamHI-EcoRl DNA fragment carrying the Ptac was purified from pDR540. This fragment was ligated to BamHI-EcoR1 digested pMG404 DNA, and ampicillin resistant, chloramphenicol sensitive transformants of *E. coli* DH1 were isolated. Plasmid DNA from one such transformant was isolated, analysed by restriction enzyme digestion and shown to contain the 121bp promoter fragment inserted into the chloramphenicol resistance gene (pMG421) (FIG. 6). pMG421 DNA was digested with BamHI, treated with calf intestine alkaline phosphatase, and ligated to a 1.2 kb BamHI promoterless origin fragment isolated from pMG411. Ampicillin resistant transformants of *E. coli* DH1 were obtained when the transformation mixture was plated at either 30° C. or 42° C. At 42° C., the low copy number origin is inactive. Two distinct plasmid types were identified from the transformants (pMG415 and pMG416) (FIG. 6). pMG415 carried a single BamHI origin fragment in the correct orientation, downstream of the Ptac, whereas pMG416 carried 3 copies of the origin fragment as direct repeats, also orientated for expression from Ptac (FIG. 6).

Plasmids pMG415 and pMG416 were transformed into *E. coli* D900 (lacI$^{sq}$), a strain which overproduces the lac repressor, the controlling element of the Ptac promoter. Induction of Ptac can be effected by the addition of the lactose analogue IPTG (isopropylthiogalactoside). pMG415 transformants of D900 grown in L-broth had a low copy number as judged by agarose gel electrophoresis, but this was not increased by the addition of IPTG. pMG416 transformants of D900 grown in L-broth also had a low copy number, but this increased quickly on the addition of IPTG to the culture, demonstrating controllable copy number induction of pMG416 from Ptac.

EXAMPLE 5

The Expression of the Calf Stomach met Prochymosin Gene Cloned into a Dual-origin Plasmid (a) Construction of pMG168

To demonstrate that dual-origin plasmids were useful for the expression of cloned heterologous genes in *E. coli*, a plasmid was constructed carrying the calf stomach met-prochymosin gene. pCT70 (Emtage et al 1983) was digested with HindIII and SalI and a ~2.4 kb fragment carrying the met-prochymosin gene under Ptrp control was isolated. This fragment was ligated to two DNA fragments isolated from pMG165, the 5.6 kb SalI-PstI fragment and the 1 kb HindIII-PstI fragment (FIG. 3). The resulting plasmid (pMG168) isolated from transformants of *E. coli* DH1, comprised the cloned gene downstream of the origin of replication, such that any transcriptional read through from Pr, would lead to additional transcription of the met-prochymosin gene (FIG. 3).

Figure 7:
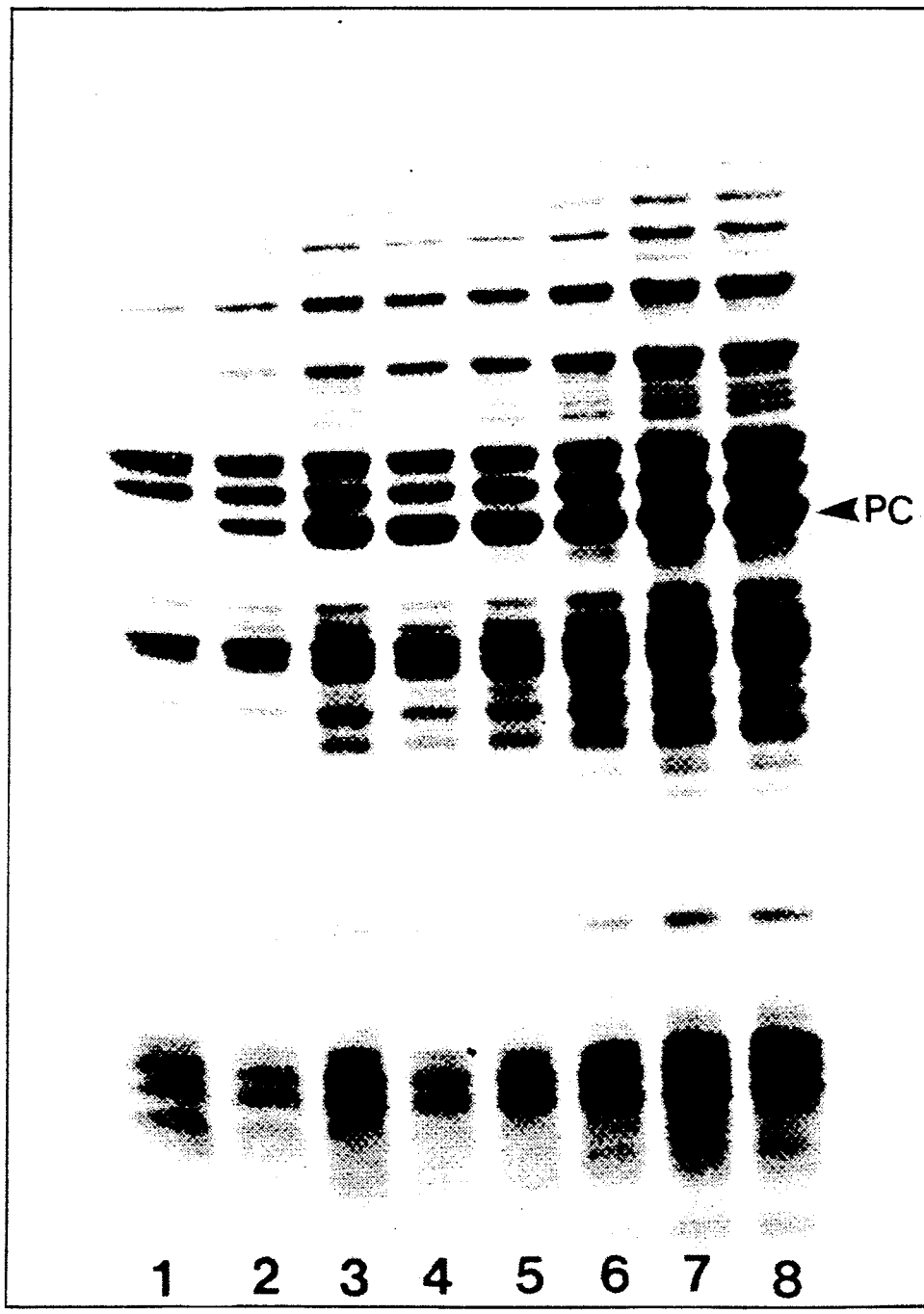
FIG. 7 is a 10% polyacrylamide gel of protein from total cell extracts prepared from E. coli E103(S) transformed by pMG169 after temperature shift treatment, samples being taken at hourly intervals (lanes 1-8, hours 0-7)

(b) Expression of met-prochymosin Protein from pMG168 pMG168 was transformed into *E. coli* E103(S) and met-prochymosin expression analysed by polyacrylamide gel electrophoresis. *E. coil* E103(S) transformants were grown in L-broth at 30° C. to an OD$_{600}$ 0.4, and shifted to 42° C. Cultures were then incubated at 37° C. with shaking, and samples removed at hourly intervals for analysis of copy number and protein expression. DNA copy number was determined as described for pMG159 and pMG165. For analysis of protein, each culture sample was centrifugal, the pellet collected and resuspended in stop buffer (1% SDS, 10 mM tris HCl pH 7.5) and an equal volume of sample buffer (0.12 M tris HCl pH 6.8, 20% glycerol, 1.2 H β-mercaptoethanol, 6% SDS) and boiled for 3 minutes. Polyacylamide gel electrophoresis, staining and destaining methods were essentially as described in Maniatis et al (1982). Stained polyacrylamide gels were scanned using a Joyce Loebl Chromoscan at 530 nm. Both DNA plasmid copy number and met-prochymosin protein levels were greatly increased following a temperature shift from 30° C. to 42° C. (Table 4, FIGS. 4 and 7).

Copy number increased rapidly during a 90 minute post induction period at 37° C., whilst met-prochymosin accumulation was more gradual. On the basis of polyacrylamide gel scanning, the recombinant gene product accumulated to at least 10% of total extractable protein by 4–5 hours after the temperature shift. Induced copy number values for pMG168 were lower than for the parent dual origin plasmid (pMG165), but still increased from 3–4 per chromosome to 120–150 per chromosome. Cell viability fell following induction of pMG168 but not of pMG165. It was concluded that this loss in viability resulted from the toxic accumulation of recombinant gene product.

TABLE 4

| Increase in Met-Prochymosin Gene Expression | |
|---|---|
| Time after Induction at 37° C. (hrs) | % Total Protein as met-prochymosin |
| 0 | <0.5 |
| 3 | 7.08$^a$ |
| 4 | 9.09$^a$ |
| 5 | 10.25$^a$ |

$^a$These measurements are from gel scans; the uninduced levels of protein are difficult to measure accurately by this method.

EXAMPLE 6

Expression of the Chloramphenicol Acetyl Transferase Gene Cloned onto a Dual Origin Plasmid (a) Construction of pMG160

Because of the limitations in the accurate quantitation of stained protein bands on polyacrylamide gels, cloned gene expression on dual origin vectors was further quantitated by assaying the increased activity of chloramphenicol acetyl transferase following copy number induction of plasmid pMG169. Plasmid pMG169 was made from pMG165 in an analagous way to the construction of pMG168 (Example 5), except that the purified HindIII-SalI fragment carried the structural gene for chloramphenicol acetyl transferase under control of Ptrp (FIG. 3).

Figure 4:
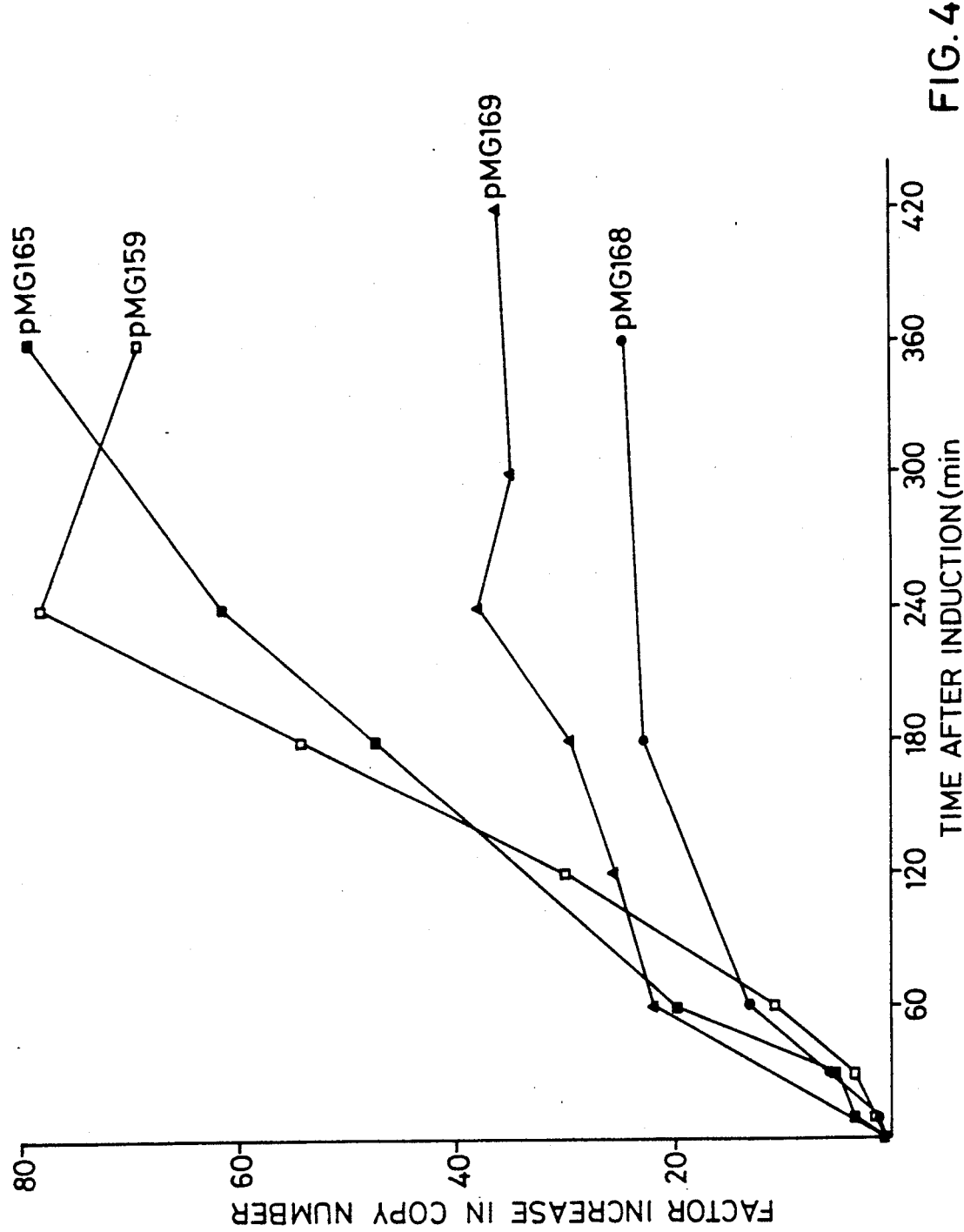
FIG. 4 is a graph of copy number induction following a temperature shift (30° C. to 42° C. with subsequent incubation at 37° C.) of transformants of E. coli carrying pMG159, pMG165, pMG168 and pMG169.

(b) Expression of Cloned Chloramphenicol Acetyl Transferase pMG169 was transformed into *E. coli* E103(S) and chloramphenicol acetyl transferase levels measured by polyacrylamide gel electrophoresis and enzyme assay (Shaw 1975). *E. coli* E103(S) transformants were grown and induced by temperature shift to 42° C., followed by continued incubation at 37° C. as described for pMG168 transformants in Example 5. Samples were removed at hourly intervals and plasmid copy number determined (FIGS. 4, 8), chloramphenicol acetyl transferase specific activities determined (Shaw 1975, Read and Northcote 1981), (FIG. 8, Table 5), and samples run on polyacrylamide gels (FIG. 9). The plasmid copy number increased with similar kinetics to that of pMG168, and with similar absolute values (FIG. 4). Chloramphenicol acetyl transferase assays demonstrated that the specific activity of the enzyme in crude extracts increased approximately 80-fold as a result of the copy number induction (FIG. 8). Calculations of the proportion of extractable protein present as chloramphenicol acetyl transferase were made from a knowledge of the specific activity of the pure protein (Table 5). Uninduced levels expressed from pMG169 represented 0.25% extracted protein, whilst after 6 hours induction this had risen to 21.9%.

TABLE 5

Increase in Chloramphenicol Acetyl Transferase Specific Activity

| Time after Induction at 37° C. (hrs) | [a]% Total Protein as Chloramphenicol acetyl transferase |
|---|---|
| 0 | 0.25 |
| 1 | 5.6 |
| 2 | 15.5 |
| 3 | 18.1 |
| 4 | 18.5 |
| 5 | 21.4 |
| 6 | 21.9 |
| 7 | 20.9 |

[a]These values were calculated from the known specific activity of pure chloramphenicol acetyl transferase (195 units per mg protein).

EXAMPLE 7

Plasmid Stability Studies of Dual Origin Plasmids

Plasmids pMG165 and pMG168 were transformed into *E. coli* RV308, and pMG168 into *E. coli* E103(S) to study their stability at 30° C. under conditions of chemostat growth without antibiotic selection. All experiments were started from a single colony of the appropriate *E. coli* strain, taken from an antibiotic-containing agar plate and inoculated into 100 mls of L-broth in a 250 ml conical flask with steel spring baffle. The culture was incubated in an orbital shaker (37° C. 240 rpm) until stationary phase was reached. The cells were harvested, resuspended in sterile defined medium minus glucose and inoculated into a fermenter vessel. The defined medium was glucose 4 g$l^{-1}$; [NH$_4$/$_2$SO$_4$ 5 g$l^{-1}$; Na$_2$HPO$_4$ 7 g$l^{-1}$; KH$_2$PO$_4$3 g$l^{-1}$; proline 200 mg $l^{-1}$; leucine, 100 mg $l^{-1}$; thiamine 10 mg $l^{-1}$; MgSO$_4$.7H$_2$O 200 mg $l^{-1}$, CaCl$_2$.6H$_2$O, 5 mg $l^{-1}$, ZnSO$_4$.7H$_2$O 20 mg $l^{-1}$ MnSO$_4$.4H$_2$O 2 mg $l^{-1}$, 2 mg $l^{-1}$; CuSO$_4$.5H$_2$O, 5 mg $l^{-1}$, CoCl$_2$.6H$_2$O, 0.5 mg $l^{-1}$; FeSO$_4$.7H$_2$O 100 mg $l^{-1}$; NaCl 200 mg $l^{-1}$; EDTA Na$_2$ 600 mg $l^{-1}$; NaOH 150 mg $l^{-1}$]. This medium was supplemented with tryptophan 100 mg $l^{-1}$ unless otherwise stated. Anti-foam (polypropylene-glycol 2000) was present in the medium at 0.001% v/v. The fermenter cell population was allowed to grow as a closed batch system until the biomass was at least 60% of the maximum supported by the medium. The pump was then turned on and the system run as a chemostat. When the total biomass in the fermenter was constant, it was assumed that the initial transient growth phase had ceased and thereafter the number of generations in the steady state was calculated using the formula, n(number of generations)=$\mu$t/ln2 where $\mu$=growth rate which is equal to the dilution rate under steady state conditions, and t=time.

Samples were withdrawn from the continuous cultures, diluted and plated onto L-agar. 100 single colonies were picked onto both antibiotic supplemented agar and L-agar as a control. The number of colonies resistant to the antibiotic was expressed as a percentage of the number growing on the L-agar plate, and taken as representing the proportion of the population carrying the plasmid. Samples were removed periodically and plasmid DNA preparations made and analysed for any gross alterations.

Chemostat analysis of stability of pMG165 and pMG168 in *E. coli* RV308 have demonstrated that these plasmids are completely stable for at least 68 generations (Table 6) with tryptophan in the medium. Under these conditions transcription of met-prochymosin gene on pMG168 was repressed.

TABLE 6

| E. coli Strain | Plasmid | Plasmid Stability Stability % | Number of Generations +Trp | Number of Generations −Trp |
|---|---|---|---|---|
| RV308 | pMG165 | 100 | 72.5 | 30 |
| RV308 | pMG168 | 100 | 68 | 30 |
| E103(S) | pMG168 | 100 | 20 | — |

Stability analysis is still in progress for growth in the absence of tryptophan, but after 30 generations no plasmid loss has been detected. Stability analysis of pMG168 in *E. coli* E103(S) is still in progress but after 20 generations no plasmid loss had been observed. The dual-origin plasmids appear to be stable under conditions of low copy number, DNA replication being directed from the par+, pSC101 origin.

REFERENCES

Emtage, J. S., Angal, S., Doel, M. T., Harris, T. J. R., Jenkins, B., Lilley, G. and Lowe, P. A. Proc Natl Acad Sci U.S.A. 80 (1983) 3671-3675.

Hashimoto-Gotoh, T., Franklin, F. C. H., Nordheim, A. and Timmis, K. N. Gene 16 (1981) 227-235.

Ish-Horowitz, D. and Burke, J. F. Nucl Acids Res 9 (1981) 2989-2998.

Maniatis, T., Fritsch, E. F. and Sambrook, J. Molecular Cloning Cold Spring Harbor Laboratory (1982).

Queen, C. J Mol and Applied Genet 2 (1983) 1-10.

Read, S. M. and Northcote, D. H. Analytical Biochem 116 (1981) 53-64.

Russell, D. R. and Bennett, G. N. Gene 20 (1982) 231-243.

Sanger, F., Nicklen, S. and Coulsen, A. R. Proc Natl Acad Sci U.S.A. 74 (1977), 5463-5467.

Shaw, W. V. Methods in Enzymology 43 (1975) 737-755.

Tatchell, E., Nasmyth, K. A. and Hall, B. D. Cell 27 (1981) 25-35.

| List of *Escherichia coli* strains-mentioned in the Examples | | |
|---|---|---|
| Strain | Genotype | Reference or Source |
| DH1 | F−, recA1, endA1, gyrA96, thi-1, hsdR17(r$_k$−, m$_k$+) supE44, λ− | Maniatis et al (1982) |
| HB101 | F−, hsdS20(r$_B$−, m$_B$−), recA13, ara14, proA2, lacY1, galK2, rpsL20, (Sm$^r$), xyl-5, mtl-1, supE44, λ− | Maniatis et al (1982) |
| RV308 | λ−, F−, Sm$^r$, gal305 | [a]ATCC 31608 |
| D900 | F'i$^q$, Zp−, proA+B+/laci+, laco+, lacZ+, lacy−, proB−, Sm$^r$. | J. R. Sadler (Denver, USA) |

-continued

List of *Escherichia coli* strains-mentioned in the Examples

| Strain | Genotype | Reference or Source |
|---|---|---|
| QY7 | F⁻, lac$_{am}$, trp$_{am}$, λbio256-cI$_{857}$ΔH1, ΔuvrB. | S. Brenner (Cambridge UK) |
| E103S | — | L. D. Simon (New Jersey, USA) |

$^a$ATCC is the American Type Culture Collection designation.

The present invention makes possible the creation of a new kind of plasmid in which the copy number can be deliberately controlled by regulatable promoters such as $P_L$ or $P_R$.

The presence of the XhoI linker 30 base pairs from the 5' end of RNA II allows the replacement of the natural promoter for RNA II by other promoters. Thus, plasmid pMG404 put RNA II under the control of the kanamycin resistance gene promoter on the plasmid pHSG415 it is believed that both origins in pMG404 function, the temperature sensitive pSC101 origin from pHSG415 and the ColE1 origin under control of the Km$^R$ promoter. Although the exact point of DNA initiation has not been determined in these plasmids, the functioning of the hybrid origin is indicated by the higher copy number of pMG404 than pHSG415, and the replication of pMG404 at 42° C. The construction of pMG410, a recircularised BalI fragment carrying the hybrid origin but not the pSC101 temperature sensitive origin, is additional evidence that the hybrid origin is functional.

The properties of pMG404 demonstrate that the RNA II promoter and the first 30 bases of RNA II can be replaced by another promoter without abolishing the initiation of DNA replication. However the Km$^R$ promoter is constitutively expressed and it is not therefore possible to alter the copy number of pMG404. Several well-defined controllable promoters exist which function in *E. coli*; the $P_L$ promoter from bacteriophage λ was used to construct plasmid pMG411, with a ColE1 hybrid origin under direct control. pMG411 retained the origin from pHSG415, and was maintained at a low copy number at 30° C. in a strain carrying a ts λ repressor gene (QY7). When the λ repressor was inactivated at 42° C., the copy number increased, indicating that replication of the ColE1 origin was being driven by $P_L$. It is therefore clear that the copy number of such plasmids can be deliberately controlled from regulated promoters and this opens the way to constructing plasmids whose copy number can be controlled either by temperature (as with $P_L$ in pMG411) or more importantly by the alternation of the concentration of metabolites such as tryptophan or lactose.

We claim:

1. A DNA vector for use in procaryotic host cells comprising to replication systems that function in the same host cell; a first origin of replication resulting in a low copy number and stable inheritance of the vector, and a second, high copy number, origin of replication at which replication is directly controllable as the result of replacement or alteration by DNA manipulation of the natural vector sequence(s) which control replication at said second origin.

2. A vector according to claim 1, wherein the copy number of the controllable origin of replication is controlled by temperature.

3. A vector according to claim 1 wherein the controllable origin of replication is derived from a naturally occurring high copy number plasmid having a copy number control system involving transcriptional control by RNAII or a similar RNA species.

4. A DNA vector for use in procaryotic host cells comprising two replication systems that function in the same host cell; a first origin of replication resulting in a low copy number and stable inheritance of the vector, and a second, high copy number, origin of replication at which replication is directly controllable as the result of replacement or alteration by DNA manipulation of the natural vector sequence(s) which control replication at said second origin of replication, wherein the second, high copy number, origin of replication is a replication system comprising an origin of replication and an associated DNA sequence encoding an RNA species which provides a primer or initiation factor which initiates DNA replication by formation of a complex at or near the origin of replication, in which transcription of said RNA species is directly controllable such that, when host cells carrying the vector are propagated under selected conditions, replication takes place at a high copy number from the origin.

5. A vector according to claim 4 wherein the natural promoter which promotes transcription of the RNA species is replaced by a promoter that is controllable by external stimulus.

6. A vector according to claim 5 wherein the promoter that is controllable by external stimulus is the $P_L$ promoter, $P_R$ promoter, $P_{re}$ promoter, $P_{rm}$ promoter, $P'_R$ promoter, T7late promoters, trp promoter, tac promoter, lac promoter, gal promoter, ara promoter or recA promoter.

7. A vector according to claim 4 wherein transcription of the RNA species is controlled by incorporating a regulating function into the replication system.

8. A vector according to claim 7 wherein said regulating function comprises the lac operator or the $O_L$ or $O_R$ operator of phage lambda.

9. A method for producing a vector according to claim 1 comprising including in the DNA sequence coding for the second replication system a DNA sequence which permits direct control of replication at the second origin.

10. A process for the production of a gene product comprising transforming procaryotic host cells with a DNA vector according to claim 1, said DNA vector containing a gene sequence coding for production of said gene product, propagating said transformed cells under a first set of conditions in which replication takes place at low copy number mainly from the first origin of replication, and the propagating said transformed cells under a second set of conditions in which replication take place at high copy number also from the second origin of replication and the expression of said gene product is induced.

11. A process according to claim 10 for the production of preprochymosin, met-prochymosin or met-chymosin.

12. A process according to claim 10 or claim 11 in which the expression of the gene product is under the control of a promoter which is regulated by cytoplasmic levels of a repressor.

13. A process according to claim 12 wherein the synthesis of the repressor is autoregulated.

14. A process according to claim 13 wherein the promoter/repressor system is that of the tryptophan operon.

15. Plasmids pMG411, pMG159, pMG165, pMG427, pMG415, pMG416, pMG168 and pMG169.

16. A vector according to claim 1 wherein the copy number of the controllable origin of replication is controlled by at least one metabolite or metabolite analogue.

17. A process according to claim 10 wherein under said first set of conditions replication takes place exclusively from said first origin of replication.

18. A process according to claim 10 wherein under said second set of conditions replication takes place exclusively from said second origin of replication.

* * * * *